(12) United States Patent  
Bauer et al.

(10) Patent No.: US 7,994,655 B2
(45) Date of Patent: Aug. 9, 2011

(54) MECHANICAL, ANATOMICAL HEART-PUMPING ASSIST

(75) Inventors: Peter T. Bauer, West Linn, OR (US); Paul Erne, Horw (CH)

(73) Assignee: Inovise Medical, Inc., Portland, OR (US)

( * ) Notice: Subject to any disclaimer, the term of this patent is extended or adjusted under 35 U.S.C. 154(b) by 549 days.

(21) Appl. No.: 12/214,443

(22) Filed: Jun. 18, 2008

(65) Prior Publication Data

US 2009/0048640 A1    Feb. 19, 2009

Related U.S. Application Data

(60) Provisional application No. 60/965,188, filed on Aug. 17, 2007.

(51) Int. Cl.
*A61N 1/00* (2006.01)
(52) U.S. Cl. .......................................................... 307/42
(58) Field of Classification Search .................. 601/41; 607/14, 20, 42, 5, 119; 623/3.12
See application file for complete search history.

(56) References Cited

U.S. PATENT DOCUMENTS

| 5,056,519 | A | 10/1991 | Vince |
| 5,344,438 | A | 9/1994 | Testerman et al. |
| 5,358,519 | A * | 10/1994 | Grandjean .................... 623/3.12 |
| 6,312,399 | B1 * | 11/2001 | Lurie et al. ........................ 601/41 |
| 6,398,744 | B2 | 6/2002 | Bystrom et al. |
| 6,408,205 | B1 | 6/2002 | Renirie et al. |
| 6,772,008 | B2 | 8/2004 | Zhu et al. |
| 6,912,419 | B2 | 6/2005 | Hill et al. |
| 7,070,568 | B1 | 7/2006 | Koh |
| 7,094,207 | B1 | 8/2006 | Koh |
| 7,155,278 | B2 | 12/2006 | King et al. |
| 7,179,229 | B1 | 2/2007 | Koh |
| 7,184,829 | B2 | 2/2007 | Hill et al. |
| 7,195,013 | B2 | 3/2007 | Lurie |
| 2004/0044373 | A1 * | 3/2004 | Kroll et al. ...................... 607/14 |

* cited by examiner

*Primary Examiner* — George Manuel
*Assistant Examiner* — Robert N Wieland
(74) *Attorney, Agent, or Firm* — Jon M. Dickinson, Esq.; Robert D. Varitz, Esq.

(57) ABSTRACT

A method of providing mechanical assistance to the onset of heart-pumping activity includes selecting anatomical structure adjacent the heart which may be stimulated to produce in the selected anatomical structure motion which may be delivered as driving force to the heart in relation to heart-pumping activity; control-stimulating that selected anatomical structure in a pre-determined timed relationship with respect to the normal, expected, heart-pumping onset; and by such stimulating, and utilizing the selected anatomical structure, drivingly assisting the heart-pumping onset activity.

7 Claims, 3 Drawing Sheets

US 7,994,655 B2

MECHANICAL, ANATOMICAL HEART-PUMPING ASSIST

RELATED APPLICATIONS

This application is related to and claims priority from U.S. Provisional Patent Application Ser. No. 60/965,188, filed Aug. 17, 2007, for Mechanical, Anatomical Heart-Pumping Assist, the entire contents of which are incorporated herein by reference.

FIELD OF THE INVENTION

The invention relates to medical devices for heart stimulation, and specifically to a method for treating refractory heart failure through improving left-ventricular systolic function via controlled, pacing-induced diaphragmatic stimulation (PIDS) effected either directly, or as a consequence of phrenic nerve stimulation (PNS).

BACKGROUND OF THE INVENTION

Patients having severe congestive heart failure (CHF), such as class III and IV on the New York Heart Association (NTHA) scale, may become refractory, i.e., resistant, to standard medical therapy. One factor which may contribute to such resistance is renal insufficiency with renal perfusion.

A number of device-based therapies have been developed to prevent the progression of heart failure and to improve systolic function in patients suffering from CHF, as is well known to those of ordinary skill in the art. One therapy is cardiac resynchronization therapy (CRT), which has proven to be an effective method to decrease morbidity and mortality, and to increase quality of life in patients with severe to moderate heart failure and mechanical dyssynchrony. The implantation of a biventricular pacemaker in such patients leads to a more synchronous, simultaneous contraction pattern of the right and left ventricles, and, assuming proper placement of the ventricular pacing lead and optimized pacemaker settings, results in an improvement in systolic performance of the heart, which can be measured as improvements in left ventricular ejection fraction, end-diastolic volume, end-systolic volume, and end-diastolic pressure. So called reverse remodeling may not only be achieved by CRT, but also through other methods, depending on the underlying root cause for the severe systolic dysfunction and the benefit those methods offer with respect to the treatment of those specific root causes, left ventricular assist devices (LVAD) for patients with severely failing hearts who are waiting for heart transplants, cardiac contractility modulation (CCM) with very low systolic strength and no dyssynchrony, and external counter pulsation therapy (ECPT) to name a few conditions.

While cardiac rhythm management devices, e.g., CRT, are proven effectively to improve systolic function, electrical stimulation of the heart through internal electrodes, however, may also cause unwanted stimulation of skeletal muscle.

Referring briefly to FIG. 1, a patient's chest cavity is depicted generally at 10. In cavity 10 is contained the patient's heart 12, right lung 14 and left lung 16. The left phrenic nerve 18, which provides innervation for the diaphragm 20, arises from the cervical spine and descends to diaphragm 20 through the mediastinum 22 where the heart is located. As it passes heart 12, left phrenic nerve 18 courses along the pericardium 24, superficial to the left atrium 26 and left ventricle 28. Because of its proximity to any electrodes used for pacing, the phrenic nerve may be stimulated by a pacing pulse, i.e., phrenic nerve stimulation (PNS), The resulting involuntary contraction of the diaphragm may be quite annoying to the patient, resulting in a spasm similar to a hiccup. PNS has been reported in about a quarter of patients having implanted CRT devices.

PIDS/PNS is intended to cause contraction of the diaphragm, and may be accomplished by an invasive implantation of electrode(s), may be accomplished by stimulation through percutaneous pathways, or by placement of electrodes on the surface of the human body.

While PIDS/PNS may have painful side effects and other undesirable symptoms, it remains an effective tool for controlling respiration, for providing utility in the acute and chronic treatment of breathing disorders, and for controlling respiration during medical procedures. A diaphragmatic pacemaker is described in U.S. Pat. No. 5,056,519 for Unilateral diaphragmatic pacer to Vince, granted Oct. 15, 1991.

Other uses of implantable or cutaneous-based medical stimulations devices are known to those of ordinary skill in the art.

SUMMARY OF THE INVENTION

A method of providing mechanical assistance to the onset of heart-pumping activity includes selecting anatomical structure adjacent the heart which may be stimulated to produce in the selected anatomical structure motion which may be delivered as driving force to the heart in relation to heart-pumping activity; control-stimulating that selected anatomical structure in a pre-determined timed relationship with respect to the normal, expected, heart-pumping onset; and by such stimulating, and utilizing the selected anatomical structure, drivingly assisting the heart-pumping onset activity.

It is an object of the invention to provide a method of managing cardiac rhythm by periodic stimulation of the diaphragm, either directly, or through such stimulation of a patient's phrenic nerve.

This summary and objectives of the invention are provided to enable quick comprehension of the nature of the invention. A more thorough understanding of the invention may be obtained by reference to the following detailed description of the preferred embodiment of the invention in connection with the drawings.

BRIEF DESCRIPTION OF THE DRAWINGS

In FIGS. 2 and 3 stimulation connections for both PIDS (direct to diaphragm; and PNS (direct to phrenic nerve) are shown.

DETAILED DESCRIPTION OF THE PREFERRED EMBODIMENTS

The basic concept of this invention is to use timed stimulation of the phrenic nerve in order to effect, through that stimulation, mechanical pulse activity in the diaphragm, which activity is useful to provide pumping assist to the heart at the onset of a heart-pumping cycle. In a broad sense, the invention contemplates using electrical stimulation of some appropriate anatomical structure, such as a selected portion directly of the diaphragm, or of the diaphragm via the phrenic nerve, which structure is capable of producing a mechanical impulse that is deliverable at the appropriate location, or locations, to the heart for the purpose of assisting, in an appropriately timed fashion, the beginning of blood pumping in a heart-pumping cycle. We will refer to this stimulation both, and interchangeably, as pacing-induced diaphragmatic stimulation (PIDS), mentioned above, and as phrenic nerve stimulation (PNS), also mentioned above. It should be understood that such reference consistently applies alternately, and in combination, to both specific locations of stimulation.

PIDS/PNS may be used to enhance the systolic performance of the heart, if the amplitude of the stimulation and the timing of the pulse with respect to the intrinsic or paced activation of the left and right ventricles, are well controlled in either an open or closed control loop.

One key element of control is stimulation-amplitude control. Specifically, this control should manage such stimulation amplitude so as to avoid "crossing" a patient's pain threshold by holding such amplitude to a level aimed at producing no more than asymptomatic PIDS/PNS, rather than more problematic symptomatic PIDS/PNS. The specific appropriate amplitude level may differ from patient to patient, and is readily determined at the time of stimulation establishment by a responsible physician, clinician, etc. Accordingly, except in a circumstance where implementing the stimulation practice of the invention regardless of stimulation amplitude critically outweighs guarding against patient discomfort, a feature of the invention involves applying stimulation at a level which substantially only produces asymptomatic PIDS/PNS. An open control loop appears to furnish the best approach to accomplishing this.

Another key element of the control is to choose a hemodynamic accurate and reliable control parameter. Acoustic cardiographic parameters have been determined to be ideal control parameters, although the invention may be practiced using any hemodynamic-relevant parameter which fulfills the criteria of being accurate, reliable and easily accessible for a therapeutic device, which may be implanted or external, in an open or closed loop control approach, i.e., cardiac and/or thoracic impedance, blood temperature, blood pH value, blood pressure, right/left ventricular pressure accessed through miniature sensors in the ventricles or adjacent chambers/blood vessels.

Figure 1:
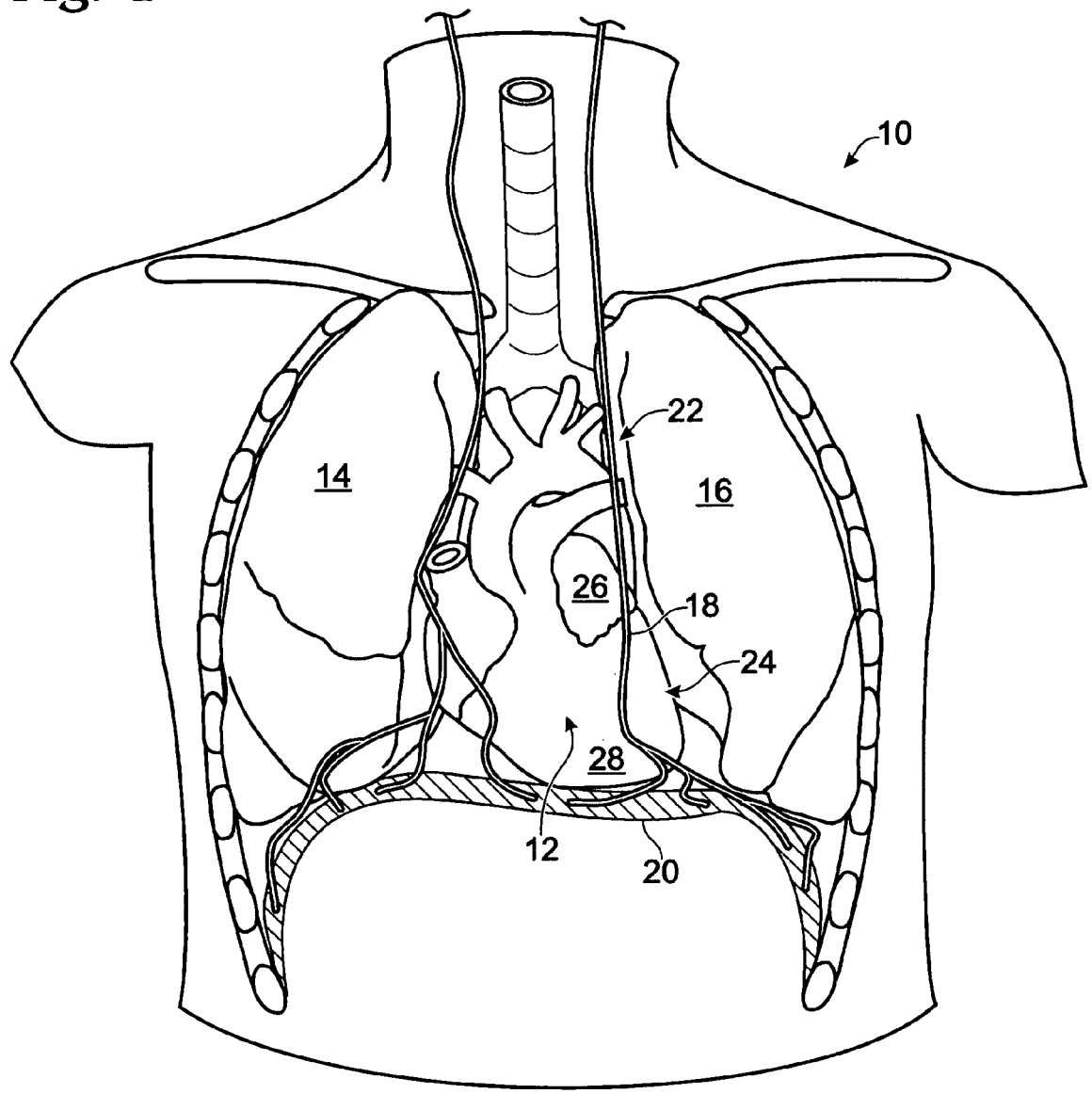
FIG. 1, mentioned briefly above, depicts a human chest cavity.
Figure 2:
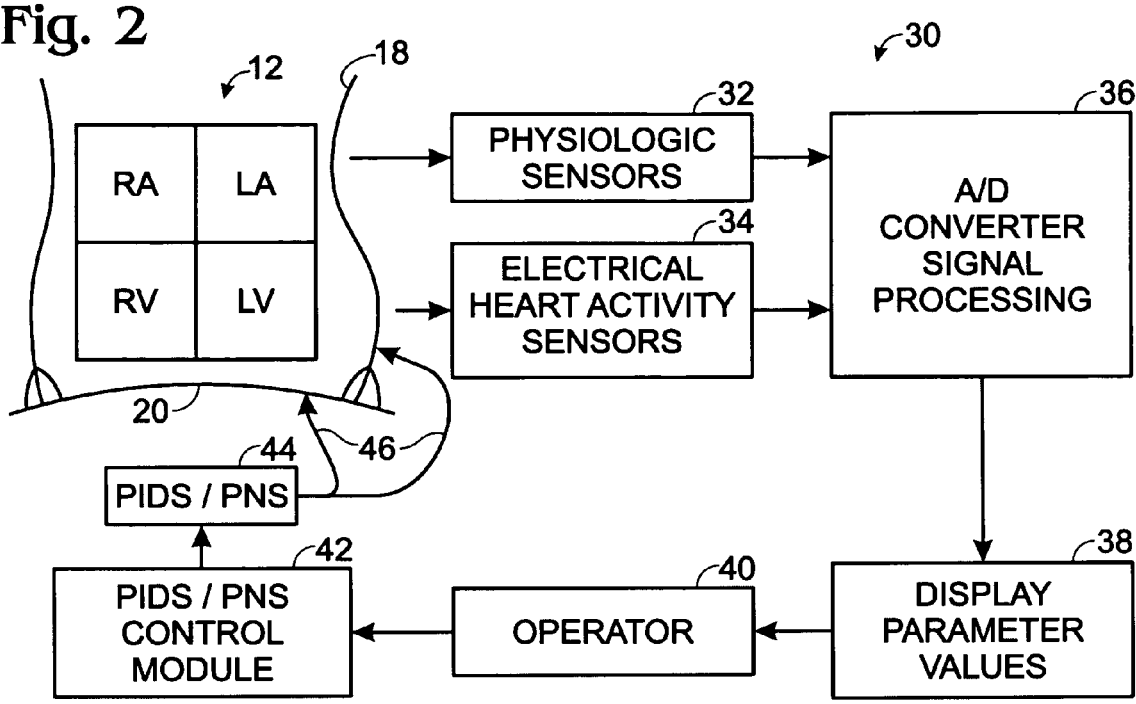
FIG. 2 depicts a block diagram of a first embodiment of the method of the invention.

Initially, and now referring to FIG. 2, an open-loop embodiment of a portion of the method of the invention is depicted generally at 30. This embodiment uses inputs from sensors to determine appropriate PIDS/PNS parameters. Two types of inputs are used: physiologic sensor inputs 32, e.g., heart sounds, impedance, blood pressure, etc.; and electrical heart activity sensor inputs 34, e.g., ECG, IEGM. Sensor inputs from both types of sensors are input to an analog-to-digital converter and signal processor 36. Output from the signal processor are displayed 38 to depict physiologic parameter values and timing delay between Q signals (ECG/IEGM) and PIDS/PNS. An operator 40 adjusts the time delay between Q signals and PIDS/PNS signals, and also adjusts PIDS/PNS amplitude. A PIDS/PNS control module 42 controls a PIDS/PNS stimulator 44, which is connected to either an implanted lead or an external stimulation lead, responds to the time delay and PIDS/PNS amplitude and provides electrical stimulation to the PNS leads 46. This provides stimulation causing the patient's natural diaphragm to contract, thus assisting heart pumping.

Figure 3:
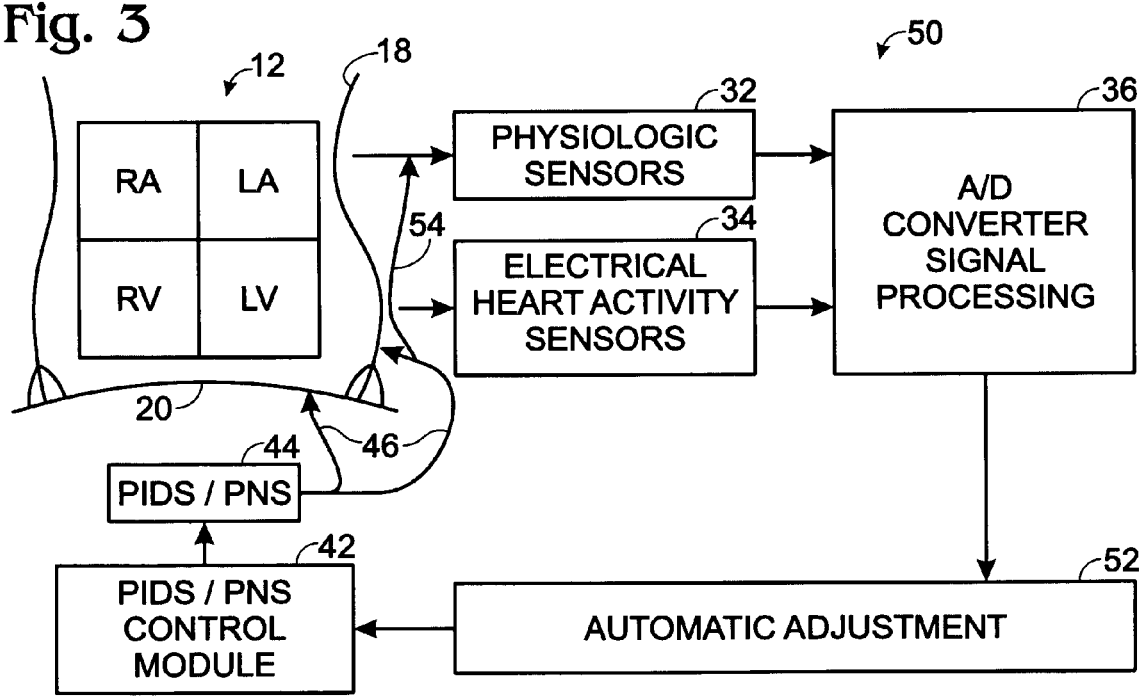
FIG. 3 depicts a block diagram of a second embodiment of the method of the invention.

FIG. 3 depicts the second embodiment, which is a closed-loop system 50. The sensors and PIDS/PNS stimulator are essentially the same as in the open-loop system, however, in place of the display and operator, a programmable device is used to automatically adjust 52 the time interval between physiologic sensors and electrical heart activity sensors and the PIDS/PNS. Also, PIDS/PNS stimulation signals are fedback into the external sensors 54.

Figure 4:
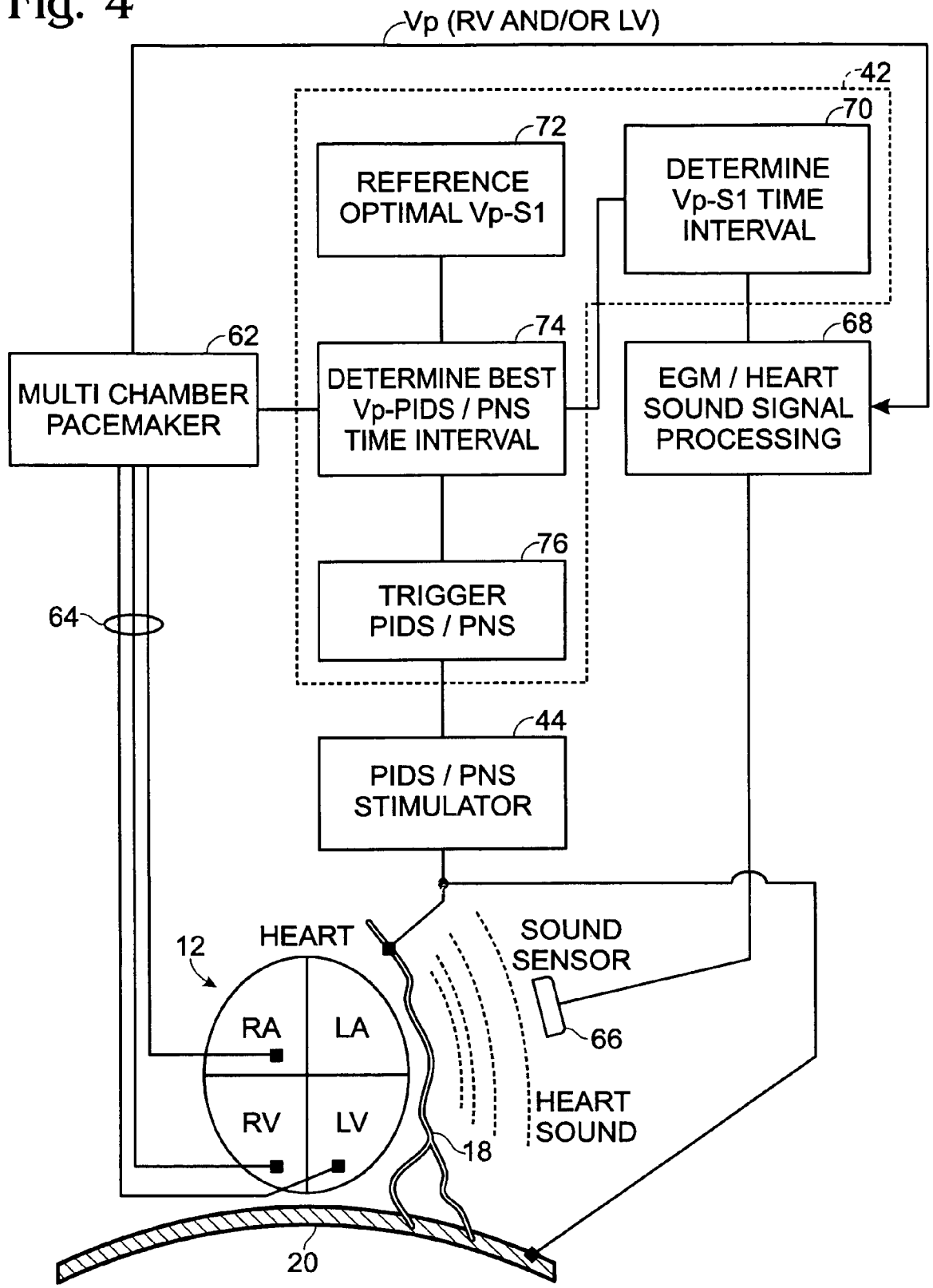
FIG. 4 depicts a system diagram using ECG and heart sound-related information to set a timing interval for the method of the invention.

FIG. 4 depicts the method of the invention 60 in terms of activating PIDS/PNS 44 used in the method of the invention. Assuming that the patient's heart 12 has been fitted with an implantable, multi-chamber, pacemaker 62, which both senses and paces heart rhythm, connected to heart 12 by pacing leads 64, and that a heart sound monitor 66 is provided, signals are transmitted from the pacemaker to a PIDS/PNS control module 42. Simultaneous signals are transmitted to the PIDS/PNS control module from the sound sensor through its signal processing components 68, which signals may be combined with those from the pacemaker. Generally, the pacemaker $V_P$ (RV and/or LV) signals are used in the method of the invention.

The combined heart sound and pacemaker signals are manipulated in PIDS/PNS control module 42 to determine $V_P$–S1 time interval 70 (or alternatively, the Q–S1 time interval which could be labeled instead in block 70), which is compared to a reference optimal $V_P$–S1 value 72 to determine a best $V_P$–PIDS/PNS time interval 74. Based on the best $V_P$–PIDS/PNS time interval, PIDS/PNS 44 is triggered, and an appropriate PIDS/PNS signal 76, having both a time interval function and a PIDS/PNS amplitude value, provides stimulation via direct connection 78 to left phrenic nerve 18.

To summarize the method of the invention, a method of providing mechanical assistance to the onset of heart-pumping activity includes selecting anatomical structure adjacent the heart which may be stimulated to produce in the selected anatomical structure motion which may be delivered as driving force to the heart in relation to heart-pumping activity. In the preferred embodiment of the method of the invention, stimulation is provided either directly to the diaphragm, or indirectly to the diaphragm via the left phrenic nerve to instigate motion in the patient's diaphragm, thus assisting in pumping by the patient's heart. The method of the invention further includes control-stimulating that selected anatomical structure in a pre-determined timed relationship with respect to the normal, expected, heart-pumping onset, as described in conjunction with FIGS. 2-4, thereby utilizing the selected anatomical structure for, drivingly assisting the heart-pumping onset activity.

Control-stimulating of the selected anatomical structure in the mentioned pre-determined, timed relationship with respect to the normal, expected, heart-pumping onset includes setting an optimal timing delay between an electric stimulus to the selected anatomical structure and specific electro-mechanical events in the patient's cardiac cycle as a function of a hemodynamic parameter. The hemodynamic parameter includes electrocardiogram parameters, heart sound parameters, intracardiac impedance measurements, thoracic impedance parameters, intracardiac pressure parameters, intravascular pressure parameter.

A modification of the method of the invention includes determining the pre-determined timed relationship as a function of physiology sensor signals and electrical heart activity sensor signals, and control stimulating only when physiology sensor signals exceed a pre-determined threshold.

A further modification of the method of the invention involves modifying the optimal timing delay as a function of patient body parameters, such as metabolic parameters, circadian rhythm parameters, motion and posture parameters, and blood flow and blood pressure in the patient's cardiovascular system.

In all practices of the invention, and for the reason stated above herein, stimulation amplitude is preferably controlled so as to produce only asymptomatic PIDS/PNS.

Thus, a method for mechanical, anatomical heart-pumping assist has been disclosed. It will be appreciated that further variations and modifications thereof may be made within the scope of the invention as defined in the appended claims.

We claim:

1. A method of employing a person's natural diaphragm for providing mechanical assistance to the expected, normal onset of heart-pumping activity comprising,
    electrically control-stimulating the phrenic nerve in a pre-determined timed relationship with respect to normal, expected, heart-pumping onset,
    by said control-stimulating, producing in the natural diaphragm, via the implementation of stimulation amplitude control, a mechanical impulse which is solely an asymptomatic impulse,
    delivering the thus-produced asymptomatic impulse to the heart, and
    by said delivering, drivingly assisting the expected, normal onset of heart-pumping activity.

2. The method of claim 1 wherein said control-stimulating includes setting an optimal timing delay between the timing of an electric stimulus to the phrenic nerve and specific electro-mechanical events in the person's cardiac cycle as a function of a hemodynamic parameter.

3. The method of claim 2 wherein the hemodynamic parameter is taken from the group of hemodynamic parameters consisting of electrocardiogram parameters, heart sound parameters, intracardiac impedance measurements, thoracic impedance parameters, intracardiac pressure parameters, intravascular pressure parameters.

4. The method of claim 2 wherein said setting of an optimal timing delay is modified as a function of selected, person-specific body parameters.

5. The method of claim 4 wherein the selected body parameters include parameters taken from the group consisting of metabolic parameters, circadian rhythm parameters, motion and posture parameters, and blood flow and blood pressure in the person's cardiovascular system.

6. The method of claim 1 wherein the pre-determine timed relationship is determined as a function of physiology sensor signals and electrical heart activity sensor signals, and wherein said control stimulating occurs only when the physiology sensor signal exceeds a pre-determined threshold.

7. The method of claim 1, wherein said
    control-stimulating is preformed specifically with respect to the left phrenic nerve.

* * * * *